US 6,574,497 B1

(12) United States Patent
Pacetti

(10) Patent No.: US 6,574,497 B1
(45) Date of Patent: Jun. 3, 2003

(54) MRI MEDICAL DEVICE MARKERS UTILIZING FLUORINE-19

(75) Inventor: Stephen Dirk Pacetti, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 187 days.

(21) Appl. No.: 09/746,843

(22) Filed: Dec. 22, 2000

(51) Int. Cl.[7] ............................................. A61M 25/00

(52) U.S. Cl. ..................... 600/420; 600/435; 606/200

(58) Field of Search ............................... 600/420, 431, 600/433, 435; 606/200

(56) References Cited

U.S. PATENT DOCUMENTS

| | | | |
|---|---|---|---|
| 3,789,832 A | | 2/1974 | Damadian |
| 4,639,364 A | | 1/1987 | Hoey |
| 4,838,274 A | | 6/1989 | Schweighardt et al. |
| 5,068,098 A | | 11/1991 | Schweighardt et al. |
| 5,154,179 A | * | 10/1992 | Ratner ..................... 604/264 X |
| 5,318,770 A | | 6/1994 | White et al. |
| 5,320,100 A | | 6/1994 | Herweck et al. |
| 5,324,504 A | | 6/1994 | Roger, Jr. et al. |
| 5,362,477 A | | 11/1994 | Moore et al. |
| 5,362,478 A | | 11/1994 | Desai et al. |
| 5,422,094 A | | 6/1995 | Antich et al. |
| 5,536,491 A | | 7/1996 | Asai et al. |
| 5,725,572 A | | 3/1998 | Lam et al. |
| 5,772,982 A | * | 6/1998 | Coward ..................... 424/1.73 |
| 5,908,410 A | * | 6/1999 | Weber et al. ............... 604/280 |
| 6,001,118 A | * | 12/1999 | Daniel et al. ............... 606/200 |
| 6,017,319 A | * | 1/2000 | Jacobsen et al. ............ 600/585 |
| 6,174,330 B1 | * | 1/2001 | Stinson ................... 606/198 X |
| 6,280,385 B1 | | 8/2001 | Melzer et al. |

OTHER PUBLICATIONS

L. W. Bartels et al., "MR–guided Ballon Angioplasty of Stenosed Hemodialysis Access Grafts," *Proc. Intl. Soc. Mag. Reson. Med.* 8 (2000), p. 409.
C. Manke et al, "Stentangioplastie von Becken–arterienstenosen unter MRT–Kontrolle: Erste klinische Ergebnisse," *Fortschr Röntgenstr* (2000), 172: pp. 92–97.
E.D. Becker, "High Resolution MR," 2d Ed., Academic Press (1980) Ch. 2, pp. 9–11 and 280–283.
J.–P. Laissy et al., "Magnetic Resonance Angiography of Intravascular Endoprostheses: Investigation of Three Devices," *Cardiovasc Intervent Radiol* (1995), 18 pp. 360–366.

(List continued on next page.)

*Primary Examiner*—Kevin Lee
(74) *Attorney, Agent, or Firm*—Fulwider Patton Lee & Utecht, LLP

(57) ABSTRACT

Medical devices that incorporate compounds containing fluorine-19 materials for use as contrast agents and passive markers in interventional magnetic resonance angiography. The device may be a guidewire, guiding catheter, angioplasty catheter, stent, embolic protection device, endovascular graft, endotracheal tube, Foley catheter, Hickman catheter, Broviac catheter, cerebrospinal fluid shunt, biliary stent, stylet, biopsy needle, electrode, percutaneous or endoluminal transducer or other desired interventional medical device. The fluorine-19 material may be configured from an elastomer, a fluid, a fluorosilicone, or a perfluorocarbon grease or oil. Such materials may be incorporated into marker bands and/or stripes, or may be deposited into or dispersed within the walls or lumens of the medical device to be visualized. Use of fluorine-19 containing markers and contrast agents provide a novel method of performing angioplasty and deploying stents, grafts, embolic protection and other such devices using interventional magnetic resonance angiography.

46 Claims, 9 Drawing Sheets

OTHER PUBLICATIONS

M.R. Meiler et al., "In Vivo Oxygen Tension Mapping of RIF–1 Tumors via Fluorine–19 NMR During 5–Fluorouracil Chemotherapeutic Intervention," *Proc. Intl. Soc. Mag. Reson. Med.*, 8 (2000), p. 255.

D.J. Collins et al., "A Flexible Dual Resonant $^1$H/$^{19}$F RF Coil for In–Vivo Magnetic Resonance Spectroscopy," *Proc. Intl. Soc. Mag. Reson. Med.*, 8 (2000), p. 1417.

S.–P. Lee et al., "Rapidly Switchable RF Coil for $^{19}$F/$^1$H NMR Studies," *Proc. Intl. Soc. Mag. Reson. Med.*, 8 (2000), p. 1416.

X. Yang MD, PhD et al., "Intravascular MR–monitored Balloon Angioplasty: An In Vivo Feasibility Study," *JVIR*, vol. 9, No. 6, (Nov.–Dec. 1998), pp. 953–959.

R.A. Omary, MD et al., "MR–guided Angioplasty of Renal Artery Stenosis in a Pig Model: A Feasibility Study," *JVIR*, vol. 11, No. 3 (Mar. 2000), pp. 373–381.

M.E. Ladd et al., Interventional and Intravascular MR Angiography, *Herz*, 25 (2000), Nr. 4, pp. 440–451.

F.K. Wacker, MD et al., "Magnetic Resonance–Guided Vascular Catherization: Feasibility Using a Passive Tracking Technique at 0.2 Telsa in a Pig Model," *JMRI*, 10 (1999), pp. 841–844.

C.J. Bakker, PhD et al, "MR–Guided Balloon Angioplasty: In Vitro Demonstration of the Potential of MRI for Guiding, Monitoring, and Evaluating Endovascular Interventions," *JMRI*, (Jan./Feb. 1998), pp. 245–250.

A. Bücker et al., "Stentplazierung unter Echtzeit–MR–Kontrolle: erste tier–experimentelle Erfahrungen," *Fortschr. Röntgenstr.*, 169, 6 (1998), pp. 655–657.

Z.–P. Liang and P.C. Lauterbur, "Principles of Magnetic Resonance Imaging: A Signal Processing Perspective," *Institute of Electrical and Electronics Engineers, Inc.*, (2000), pp. 217–231.

M.A. Brown, PhD and R. C. Semelka, MD, "MRI—Basic Principles and Applications," Second Edition, *Wiley–Liss*, (1999), pp. 129–139, 141–151, 173–180.

A.C. Lardo, PhD, "Real–Time Resonance Imaging: Diagnostic and Interventional Applications," *Pediatric Cardiology*, vol. 21, (2000), pp. 80–98.

M. Wendt et al., "Visualisation, tracking and navigation of instruments for MRI–guided interventional procedures," *Min. Invas. Ther. & Allied Technol.*, vol. 8(5), (1999) pp. 317–326.

G. Adam, MD et al., "Interventional Magnetic Resonance Angiography," *Seminars in Interventional Radiology*, vol. 16, No. 1, (1999), pp. 31–37.

S.T. Kee, MD et al., "MR–guided Transjugular Portosystemic Shunt Placement in a Swine Model," *JVIR*, vol. 10, (May 1999), pp. 529–535.

R. B. Lufkin, et al., "Interventional MRI: update," *European Radiology*, vol. 7, (1997), pp. 187–200.

P.W. Stroman, PhD et al., "Will It Be Feasible to Insert Endoprostheses Under Interventional MRI?" *Journal of Endovascular Surgery*, vol. 3, (1996), pp. 396–404.

* cited by examiner

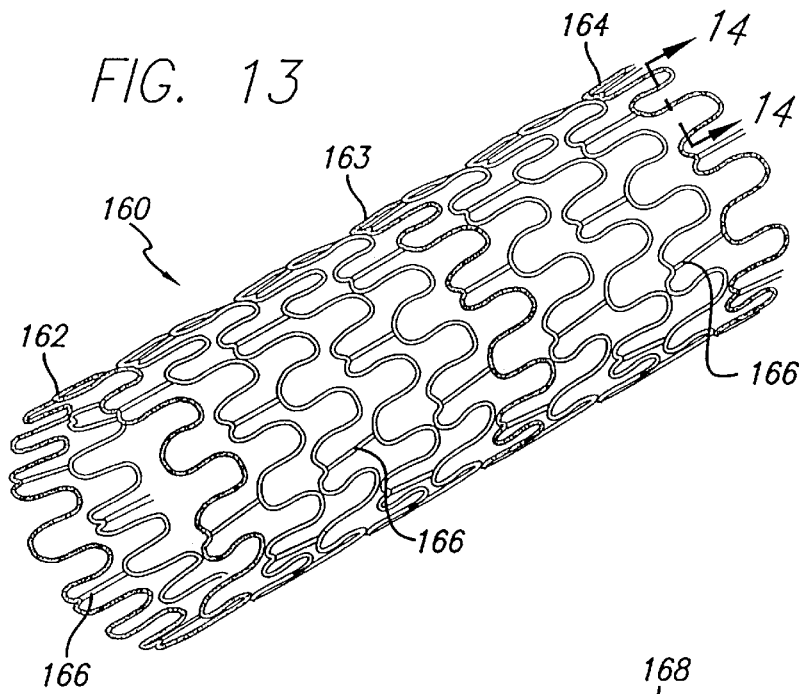
FIG. 13
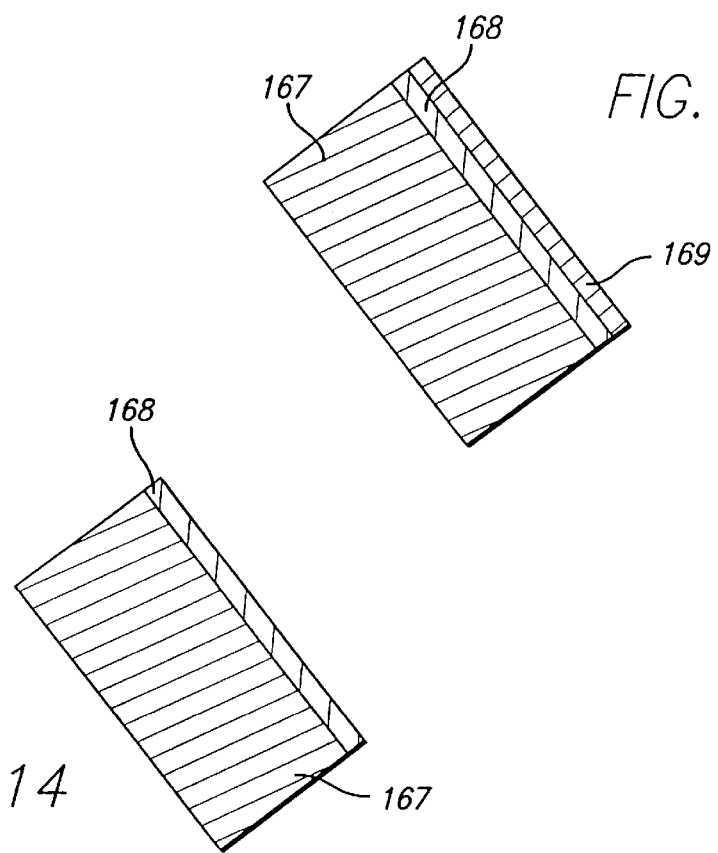
FIG. 15
FIG. 14

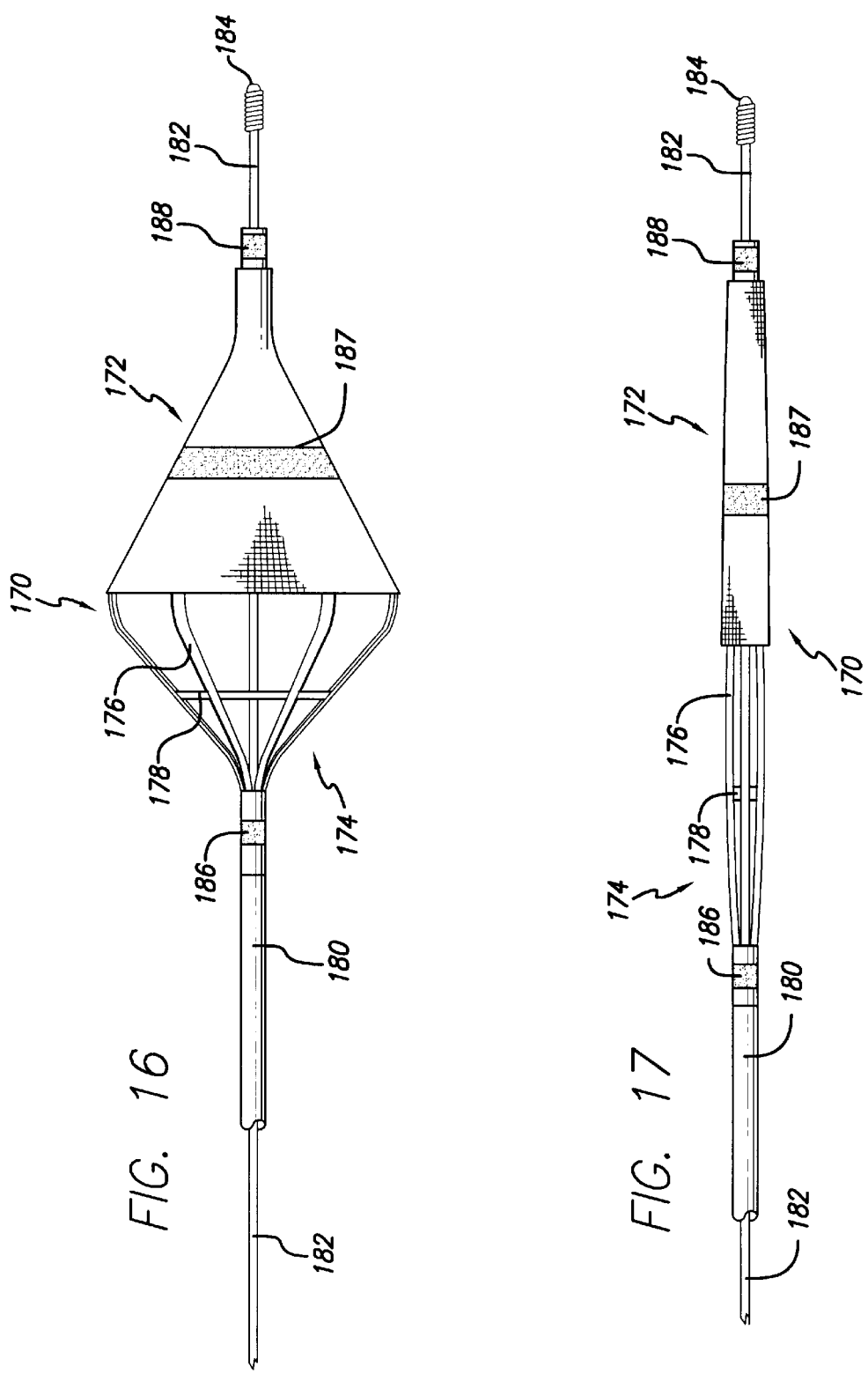

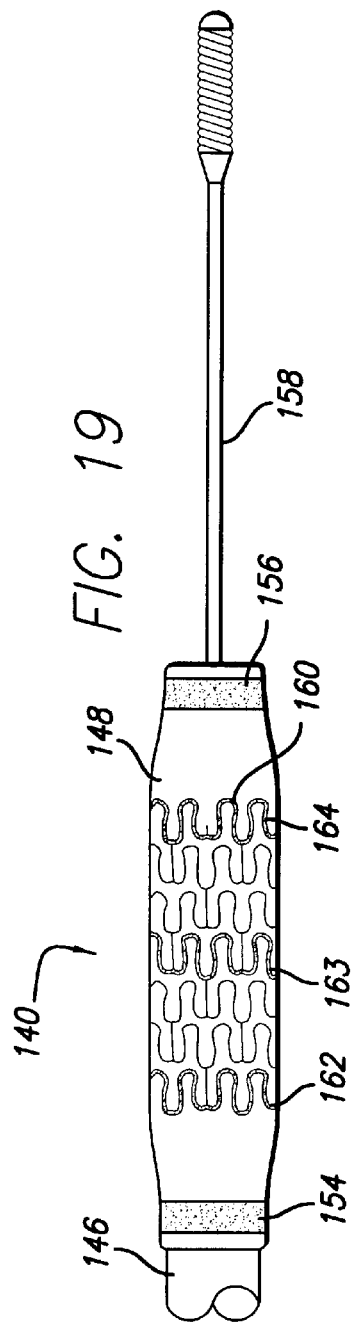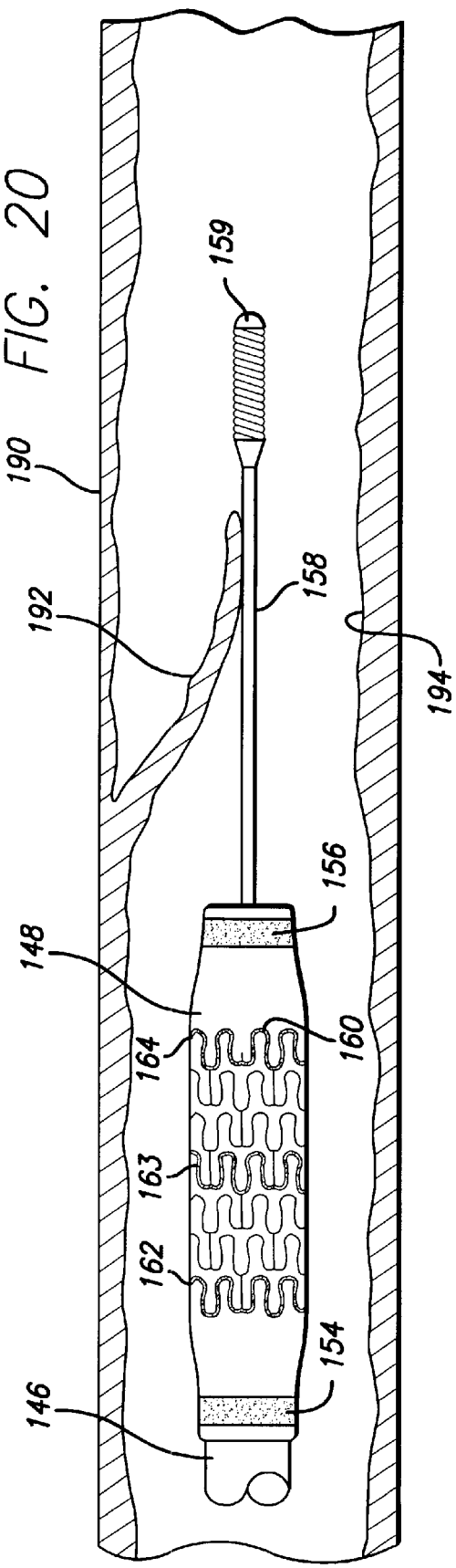

MRI MEDICAL DEVICE MARKERS UTILIZING FLUORINE-19

BACKGROUND OF THE INVENTION

The present invention relates to apparatus and methods for medical imaging, specifically to the use of passive markers for magnetic resonance imaging. In a particular, the invention relates to the use of fluorine-19 ($^{19}$F) nuclei containing compounds as contrast agents and markers for medical devices used in interventional magnetic resonance angiography.

Currently, x-ray fluoroscopy is the preferred imaging modality for cardiovascular interventional procedures. No other method, at this time, has the temporal or spatial resolution of fluoroscopy. As good as fluoroscopy is, however, it does have drawbacks. Catheterization is required in order to directly inject the high concentration of iodinated contrast agent required. Systemic administration of the contrast agent would require too high a dose of agent. Additionally, iodinated contrast agents are nephrotoxic with a real incidence of acute renal failure, particularly in patients with compromised renal function. Allergic reactivity also serves as a contraindication for certain patients. Visualization and tracking of devices under fluoroscopy is accomplished either by the device's inherent adsorption of x-rays, or by the placement of radiopaque markers. Fluoroscopy generates a compressed, two dimensional image of what are three dimensional structures. This requires multiple views to appraise complex vasculature. Moreover, fluoroscopy uses ionizing x-ray radiation with its attendant hazards. This is an issue for the patient during protracted or repeated interventions. It is a daily issue for the interventionalist who must also cope with the burden of personal dose monitoring and wearing lead shielding.

One imaging modality, which has the potential to supplant fluoroscopy, or perhaps replace it in the long term, is magnetic resonance imaging (MRI). MRI does not use ionizing radiation and does not require catheterization to image vasculature. MRI contrast agents, which are often necessary for best resolution, are much less nephrotoxic than iodinated fluoroscopy agents and are effective when administered intravenously.

One advantage of MRI is that different scanning planes and slice thicknesses can be selected without loss of resolution. This selection permits high quality transverse, coronal and sagittal images to be obtained directly. MRI has greater soft tissue contrast and tissue discrimination than computed tomography (CT) or other x-ray based imaging modalities, such as angiography. The reason for this being that in CT, the x-ray attenuation of tissues determines image contrast, whereas in MRI at least four separate variables can determine MRI signal intensity: (i) spin-lattice (longitudinal) relaxation time—$T_1$, (ii) spin-spin (transverse) relaxation time—$T_2$, (iii) proton density, and (iv) flow. MRI is presently used for diagnostic applications, but interventional magnetic resonance (iMR) angiography is an active area of research. For example, MRI guided balloon angioplasty has been performed to demonstrate feasibility. Similarly, stent placement in humans under MRI has also been demonstrated.

The technique of MRI encompasses the detection of certain atomic nuclei (those possessing magnetic dipole moments) utilizing magnetic fields and radio-frequency radiation. It is similar in some respects to x-ray computed tomography in providing a cross-sectional display of the body organ anatomy, only with excellent resolution of soft tissue detail. In its current use, the images constitute a distribution map of protons, and their properties, in organs and tissues. However, unlike x-ray computer tomography, MRI does not use ionizing radiation. The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections. MRI is, therefore, a safe non-invasive technique for medical imaging.

The hydrogen atom, having a nucleus consisting of a single unpaired proton, has one of the strongest magnetic dipole moments of nuclei found in biological tissues. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

Fluoroscopy uses contrast agents to enhance the imaging of otherwise radiolucent tissues. Not surprisingly, fluoroscopic contrast agents work by x-ray absorption. Contrast agents also exist for MRI image enhancement. They work in a different manner, and typically shorten either the $T_1$ or $T_2$ proton relaxation times, giving rise to intensity enhancement in appropriately weighted images. The most popular MRI contrast materials are $T_1$ shortening agents and, in general, paramagnetic ions of elements with an atomic number of 21 to 29, 42 to 44 and 58 to 70 have been found effective as MRI contrasting agents. Such suitable ions include chromium(III), manganese(II), iron(III), iron (II), cobalt (II), nickel (II), copper (II), praseodymium(III), neodymium(III), samarium(III) and ytterbium(III). Because of their very strong magnetic moments, gadolinium(III), terbium(III), dysprosium(III), holmium(III) and erbium(III) are preferred. Gadolinium(III) ions have been particularly preferred as MRI contrast agents.

In an MRI experiment, the nuclei under study in a sample (e.g. protons, $^{19}$F, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field. In some cases, the concentration of nuclei to be measured is not sufficiently high to produce a detectable magnetic resonance signal. Signal sensitivity may be improved by administering higher concentrations of the target nuclei or by coupling the nuclei to a suitable "probe" which will concentrate in the body tissues of interest.

As noted above, iMR angiography is an active area of research. Device tracking and visualization under MRI is necessary for MRI guided interventions. Plastic devices show up poorly under MRI. The reason is that even though the majority of polymers contain hydrogen nuclei, the resonance signals from protons in polymers are broad and chemically shifted from protons in water from which the majority of the MRI signal is derived. Polymeric catheters, for example, show up as regions of little or no signal under MRI (signal voids). Hence, there is a need for markers to track and visualize interventional devices.

MRI markers are divided into two categories, active and passive. Active markers, as the name implies, participate in the radio frequency signal transmission or reception of the scanner. This includes markers that emit an RF signal, markers that receive an RF signal and convey it to the scanner via a connection, and markers that generate their own magnetic or electrical field by application of electrical currents. The term active implies some sort of electrical circuit is involved. Conversely, passive markers use no wires or circuitry and work by several mechanisms. One scheme is to distort the magnetic field of the scanner. Another is by enhancing or modifying the signal from protons in the vicinity. Still another is by containing nuclei with their own distinct signal that is different from water or fat. Passive markers have the advantage that they are simpler and, generally, have fewer parts. They require no connection to the scanner or additional circuitry. There also may be the perception amongst physicians that active currents and voltages in or on interventional devices create additional safety issues to be managed. Lastly, passive markers are conceptually similar to the radiopaque markers in fluoroscopy, even if they work in a very different way.

There are two main types of passive markers being proposed. One is based on magnetic susceptibility. This usually includes paramagnetic or ferromagnetic particles, bands, or other components placed in or on the device. These materials perturb the magnetic field in the vicinity of the device. This alters the resonance condition of protons in the vicinity. The net result is a signal void that appears black in MRI images.

The second scheme uses the currently approved gadolinium contrast agents; however, the contrast agents are placed inside the device. For example, gadolinium contrast solution is used to fill the lumen of a catheter or inflate an angioplasty balloon. In $T_1$ weighted images, aqueous solutions of gadolinium show a signal enhancement due to the $T_1$ shortening effect of the gadolinium. Gadolinium also shortens $T_2$ and gives some enhancement in those images as well. In contrast to the susceptibility artifact which is dark, an aqueous gadolinium solution marker shows up bright.

Another mechanism is possible if the medical device contains nuclei other than protons. In this case, it is possible to track the device due to the distinctive signal of this other nuclei, especially its frequency. Protons, hydrogen nuclei, have the advantage that they are abundant and have very good MRI sensitivity. They also have only two allowed spin states (nuclear spin=½). Nuclei with a spin greater than ½ have a quadrapole dipole moment, which broadens their NMR resonance signal. Fluorine-19 has reasonable sensitivity compared to $^1H$ and a resonant frequency that can be accommodated by the RF equipment in current scanners. Fluorine-19 also has a spin quantum number of ½, like hydrogen nuclei, giving it a sharp NMR signal.

What has been needed, and heretofore unavailable, in the art of interventional magnetic resonance angiography are medical devices (such as guidewires, catheters and implantable prostheses, e.g., stents) which contain passive markers for visualization under MRI. Such medical devices should provide a visible indication of the device during iMR angiography, without reliance upon susceptibility artifacts and signal voids. The present invention satisfies these and other needs.

SUMMARY OF THE INVENTION

Briefly, and in general terms, the present invention is directed to the design and configuration of medical devices for use in interventional magnetic resonance (iMR) angiography. The medical devices of the present invention incorporate compounds that contain fluorine-19 ($^{19}F$) nuclei for use as contrast agents and passive markers. MRI guided balloon angioplasty has been performed to demonstrate feasibility. Similarly, stent placement in humans under MRI has also been demonstrated. Configuration of such medical devices with $^{19}F$ markers will enhance the viability of iMR angiography. Since the art of iMR angiography has relied on the use of gadolinium contrast agents and signal voids as passive markers, the use of contrast agents and markers containing fluorine-19 material provides a new and useful way for MRI.

A fluorine-19 containing marker may be used on any medical device which may benefit from enhanced MRI visibility. The fluorine marker of the device may encompass the device partially or wholly, meaning that the entire device may be partially, or wholly, constructed of a fluorine containing material. In addition, there may be more than one marker on the device. The device may be a guidewire, guiding catheter, angioplasty catheter, stent, embolic protection device, endovascular graft, endotracheal tube, Foley catheter, Hickman catheter, Broviac catheter, cerebrospinal fluid shunt, biliary stent, stylet, biopsy needle, electrode, percutaneous or endoluminal transducer or other desired interventional medical device. It may be a temporary or permanently implanted device. There are no limitations on the size, diameter, length or other materials of the device other than they must be MRI safe. The fluorine-19 material may be configured from an elastomer, a fluid, a fluorosilicone, or a perfluorocarbon grease or oil. It is advantageous that the fluorine-19 be incorporated in a physical form that is in a fluid, mobile state at the molecular level. This gives the fluorine-19 a sharp nuclear magnetic resonance signal. Such materials may be incorporated into marker bands and/or stripes, or may be deposited into or dispersed within the walls or lumens of the medical device to be visualized under interventional magnetic resonance angiography.

In one embodiment, a medical device including the present invention may be in the form of a balloon catheter assembly having a catheter tube having wall, an outer surface, a proximal end portion and a distal end portion. The device may further include an expandable member (balloon) associated with the distal end portion of the catheter and one more markers formed from fluorine-19 containing material. The markers may be in the form of a band or stripe formed within or disposed on the wall of the catheter. Similarly, a stent incorporating fluorine-19 containing material may be disposed on the balloon. In addition, fluorine-19 markers may be incorporated into endovascular grafts and embolic protection devices.

The use of fluorine-19 containing markers and contrast agents provides a novel method of performing angioplasty using magnetic resonance imaging. Such a method includes providing a catheter assembly including a catheter tube having an expandable member (balloon) formed on the distal end portion of the catheter and at least one marker having fluorine-19 containing material formed on the catheter tube and positioned proximate the expandable member. The distal end of the catheter is advanced to a desired location in a patient vasculature having a stenosis or other lesion. The vasculature, stenosis and the fluorine-19 containing material are visualized through magnetic resonance angiography. The balloon is inflated so as to expand the stenosis and open the vasculature, then the expandable member is contracted and the catheter and the expandable member are withdrawn from the patient vasculature. A stent mounted on a balloon catheter may be deployed in a similar manner.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 13 depicts a perspective view of an embodiment of a stent including a plurality of marker bands of the present the invention.

FIG. 14 depicts a cross-sectional view along lines 14—14 of FIG. 13.

FIG. 15 depicts an alternate view of FIG. 14, including an external layer over the marker band.

FIG. 16 depicts a longitudinal plan view of an embodiment of an expanded embolic protection device, including a plurality of marker bands of the present the invention.

FIG. 17 depicts a longitudinal plan view of FIG. 16, wherein the embolic protection device is collapsed for delivery into a corporal lumen.

FIG. 19 depicts a longitudinal plan view of a stent delivery catheter assembly, including marker bands of the present invention.

FIG. 20 depicts a longitudinal plan view of a stent delivery catheter assembly, including marker bands of the present invention, which has been positioned proximate a lesion within a cross-section of a patient's vessel.

DESCRIPTION OF THE PREFERRED EMBODIMENTS

Figure 1:
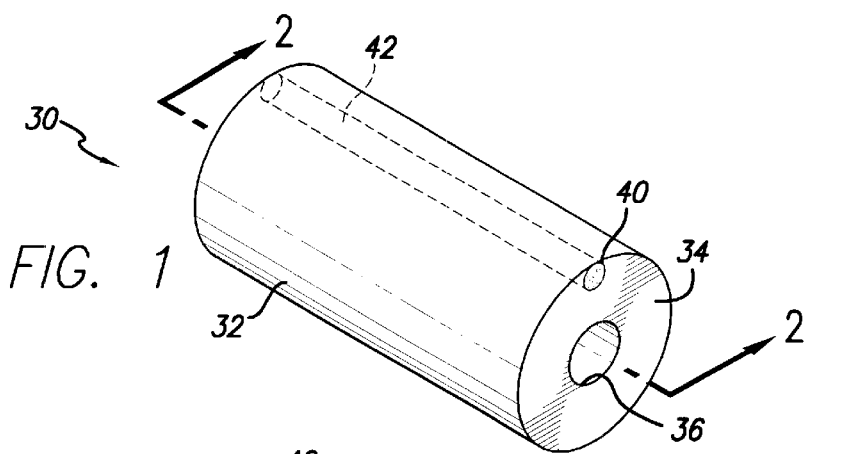
FIG. 1 depicts a partial perspective view of an embodiment of a catheter tube including an internal marker stripe of the present the invention.

As shown in the drawings for purposes of illustration, the present invention is directed to the design and configuration of medical devices for use in interventional magnetic resonance angiography. The medical devices of the present invention incorporate compounds which contain fluorine-19 ($^{19}F$) nuclei for use as contrast agents and passive markers. Interventional magnetic resonance (iMR) angiography is an active area of research. For example, MRI guided balloon angioplasty has been performed to demonstrate feasibility. Similarly, stent placement in humans under MRI has also been demonstrated. Configuration of such medical devices with $^{19}F$ markers will enhance the viability of iMR angiography.

To date, feasibility demonstrations of iMR angiography have relied on the use of gadolinium contrast agents or the signal void produced by magnetic susceptibility artifacts for the visualization of medical devices. Indeed, signal voids can make detection of a medical device possible. However, although a larger signal void enhances device detectability, the larger signal void compromises positional accuracy, as the signal void can be larger than the device. Since the signal from fluorine-19 will be distinct from a proton signal due to its frequency, it is believed that the use of contrast agents and markers containing fluorine-19 materials is a novel, useful improvement over the prior art.

Naturally occurring fluorine atoms ($^{19}F$) give a clear nuclear magnetic resonance signal, and thus can function as contrast agents or passive markers in MRI. The specific advantages for the use of $^{19}F$ include: 1) an extremely low native concentration in the body (fluorine is not naturally found in the body), 2) a high nuclear magnetic resonance sensitivity, 3) a magnetogyric ratio close to that of $^1H$, thus permitting $^{19}F$ magnetic resonance imaging to be carried out with only minor modifications of existing MRI equipment, and 4) availability of biocompatible organofluorine-containing compounds.

Since $^{19}F$ is present in the body in very low concentration, a fluorine source must be administered to a subject to obtain a measurable $^{19}F$ magnetic resonance signal. Signal sensitivity is improved by administering higher concentrations of fluorine or by coupling the fluorine to a suitable probe or contrast agent that will concentrate in the body tissues of interest. High concentrations of fluorine containing compounds must be balanced against biocompatibility and increased tissue toxicity. It is also currently believed that a fluorine agent should preferably contain magnetically equivalent fluorine atoms in order to obtain a sharp, strong signal.

A $^{19}F$ containing marker may be used on any medical device which may benefit from enhanced MRI visibility. In addition, the fluorine marker may not be just a marker at all, meaning that the entire device may be partially, or wholly, constructed of a fluorine containing material. The device may be a guidewire, guiding catheter, angioplasty catheter, stent, embolic protection device, endovascular graft, endotracheal tube, Foley catheter, Hickman catheter, Broviac catheter, cerebrospinal fluid shunt, biliary stent, stylet, biopsy needle, electrode, percutaneous or endoluminal transducer or other desired interventional medical device. It may be a temporary or permanently implanted device. There are no limitations on the size, diameter, length or other materials of the device other than they must be MRI safe.

Since the use of medical devices under MRI guidance is an area of current research, it is not known with certainty whether active tracking or passive tracking strategies will prevail. An $^{19}$F containing marker or device is a type of passive tracking. The significance of the invention is that it provides for a passive tracking mechanism to visualize devices under MRI. This scheme using fluorine nuclei involves no wires, circuits, connections, or moving parts. Since $^{19}$F has a high sensitivity, the signal has the potential to be just as strong as the signal from water in adjacent tissues. However, since it will be at a different frequency, this signal can be displayed as a different intensity, or even a different color, to the physician. The materials required are available and biocompatible. Unlike passive markers, which use magnetic susceptibility, this approach does not produce a signal void. A large signal void may be quite visible, but the visibility comes at the expense of accurately positioning the device and visualizing anatomy in close proximity of the device. Susceptibility signal voids can extend beyond the dimensions of the device, and can change in dimension depending on the orientation of the device to the magnetic field.

One question is whether a separate scan will need to be performed to image the fluorine, or if the fluorine spins can be flipped concurrently with the proton spins and the resulting signals also received concurrently. Fortunately, fluorine-19 is the only isotope of fluorine naturally present. It is also not normally present in the body. However, simply using a conventional polymer that contains $^{19}$F is not an optimum approach. To be useful, the fluorine must be in a form with a narrow range of chemical shifts. Consequently, the atoms must reside in elastomers, fluids or other rapidly rotating molecules, such as oils and greases. Fourier transform imaging techniques where a broad frequency excitation pulse is used to flip the spins could, potentially, be used to simultaneously image hydrogen and fluorine nuclei. One concern with this scheme is possibly confounding the frequency encoding scheme used to spatially locate the protons. The fluorine will resonant at a different frequency, raising the possibility that it might be confused with protons located in another part of the magnetic field gradient.

We can examine this possibility using performance specifications from a current, high performance 1.5 Tesla (T) scanner. For example, the Seimens Sonata MRI scanner has a forty centimeter field of view (FOV) and a maximum magnetic field gradient strength of forty mT/meter. At 1.5T, protons at what we will label the proximal end of the FOV will resonate at 63.86 MHz. If the maximum gradient is applied in the negative sense from this point, then at the distal end of the FOV, forty centimeters away, the proton resonant frequency will be 63.18 MHz. This frequency is still above the resonant frequency of the $^{19}$F nuclei at the proximal end of the FOV, which will have a resonance frequency of 60.08 MHz. The scanner could be programmed to interpret any signal below a certain threshold to be from $^{19}$F nuclei, and to apply different parameters for reconstructing their corresponding positions. Otherwise, a scan at the $^{19}$F frequency may need to be interleaved with the normal proton pulse sequences. This would have the drawback of lengthening the overall RF pulse train with the potential of an overall longer scanning time and possibly lower temporal resolution. However, MRI software and hardware are rapidly improving in speed.

The majority of the signal in MRI comes from water. Tissues vary in their water content but for angiography, blood is the relevant tissue. Blood is approximately 93% water. This translates into a proton concentration of 103 moles/liter. Fluorine-19 has roughly 83% the sensitivity of hydrogen, hence a fluorine-19 concentration of 125 moles/ liter will give a signal as strong as that of blood. However, MRI can image tissues with a lower water content. For example, grey matter and bone are 71% and 12% water respectively. A fluorine-19 concentration for equivalent sensitivity to these tissues is 95 and 16 moles/liter, respectively. Typical organofluorine compounds have fluorine-19 concentrations in this range. For example, perfluorooctane liquid has a fluorine-19 concentration of approximately 73 moles/ liter. The perfluoroelastomer VITON (available from DuPont) has a fluorine-19 concentration in the range of 56–76 moles/liter (depending on grade). The common fluorosilicone (polymethyl-3,3,3-trifluoro-propylsiloxane) is approximately 27 moles/liter in fluorine-19. A suitable range of fluorine-19 concentration in a marker would be 15-75 moles/liter. This also applies to configurations in which the fluorine-19 is distributed throughout the entire device. It must be noted that MRI can image proton concentrations much lower than those of blood or grey matter. Image intensity is determined by the signal to noise (S/N) ratio. Faster acquisition of data or longer acquisition times both increase the signal to noise ratio. Also, it is not a matter of visualizing the fluorine-19 marker against a tissue background generated from a proton signal. This raises the issue of the contrast between the marker, or medical device, and tissue. The fluorine-19 generates a signal at a different frequency, which is detected by the imager and can be displayed with a different intensity, color, or even separately from the tissue image.

As the fluorine-19 marker, or fluorine-19 device is imaged, the marker or device will be represented as its true shape. A useful size for a marker is determined by the visibility required and constrained by the size of the medical device itself. In MRI, the imaging volume is broken down into elements called voxels. The device or marker can be physically smaller than a voxel as it is the RF signal given off by the marker that is detected.

When imaging devices in-vitro, a MRI phantom containing suitable hydrogen atoms is typically used. Phantoms of water, blood, yogurt, mineral oil, vegetable oil, and VASE-LINE (petroleum jelly) can be found in the literature. Petroleum jelly works since its protons are in adequately rapid motion. Similarly, a perfluorocarbon grease, or partially fluorinated grease or oil can serve as a marker. Such materials are soft and may need to be encapsulated into the device. A fully contained lumen or a dispersion of the grease into the body of the device would be adequate.

Perfluorocarbon oils and fluids are readily available. A common example is the vacuum pump oil FOMBLIN (available from Ausimont), which is used in pumps that are subject to very corrosive service. Other useful fluorine containing greases and fluids include, but are not limited to: FLUORONOZ (available from TECCEM), TRIFLUNOX (available from TECCEM), GALDEN (available from Ausimont), perfluoropolyether grease, trifluoropropylsilicone fluids, fluorosilicone fluids, perfluoropolyether fluids, perfluoroalkylether fluids, perfluoroalkanes, perfluoropropane, perfluorobutane, perfluoropentane, perfluorohexane, perfluoroheptane, perfluorooctane, perfluorononane, perfluorodecane, perfluorocarbon emulsions, perfluoroalkylpolyester oils, perfluoropolyether solvent, fluorine containing freons, chlorofluorocarbons, and hydrochlorofluorocarbons.

Alternatively, bands of a fluorine containing elastomer can be affixed to a medical device for use in iMR angiography. Similarly, the elastomer could be coextruded as part of the device in the form of a strip or layer. Fluorine containing elastomers with a low glass transition temperature are available. For example, fluorosilicone is a commercially available elastomer with trifluoropropyl groups instead of methyl groups on the polymer backbone. With a glass transition temperature of less than –80° C., the fluorosilicone polymer chains are in rapid rotational motion at body temperature. Other useful fluorine containing elastomers include, but are not limited to: CHEMRAZ (available from Greene Tweed), VITON (available from DuPont), KEL-F (available from 3M), KALREZ (available from DuPont), FLUOREL (available from 3M), copolymers of vinylidene fluoride and hexafluoropropene, copolymers of chlorotrifluorethylene and vinylidene fluoride, poly (trifluoropropylmethylsiloxane), fluorosilicone elastomers, polymethyl-3,3,3-trifluoro-propylsiloxane, polymethyl-3,3, 3-trifluoropropyl-dimethylsiloxane copolymer, and perfluororesins.

Further, a fluorine containing inflation medium may be used to visualize a balloon catheter during iMR angiography. Inflation fluids are used to inflate balloon angioplasty catheters (e.g., PTCA catheters). This is currently accomplished under x-ray fluoroscopy with a radiopaque contrast agent to render the balloon more visible. A fluorine containing fluid (contrast agent) could also be used to inflate the catheter. This would render the balloon catheter visible when imaged via $^{19}$F MR imaging. Such fluids need to be very safe, as it is possible for balloons to rupture or pinhole during inflation and use. An obvious choice would be the perfluoro emulsions used as synthetic blood. One example is Oxycyte produced by Synthetic Blood International. Perfluorocarbons with a sufficiently low vapor pressure such as perfluorodecalin and perfluorotetramethylcyclohaxane are suitable for making emulsion blood substitutes. Alternatively, the marker may be formed within the material of the balloon (expandable member), or the balloon material itself may contain fluorine-19 containing compounds.

Figure 2:
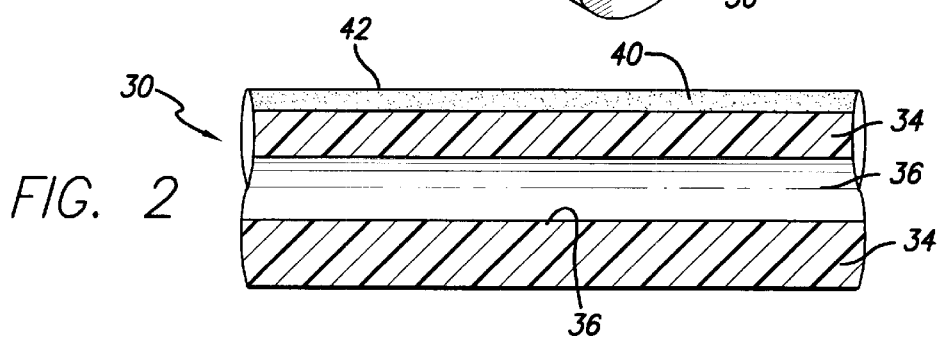
FIG. 2 depicts a cross-sectional view along lines 2—2 of FIG. 1.

The drawings show various embodiments of the present invention. Referring now to FIG. 1, an embodiment of a catheter tube 30 incorporating the present invention is shown. The catheter tube generally includes an outer surface 32 and a wall 34 forming an inner lumen 36. The catheter tube may be formed by conventional means and from conventional method and materials, such as polyesters, polyurethanes and other MRI safe materials. Since such materials generally create a signal void under MR angiography, a marker 40 is included in the catheter tube wall. As shown in FIGS. 1 and 2, the marker 40 includes a stripe 42 extending along the outer surface and parallel to the longitudinal axis of the catheter. In this first embodiment, the marker stripe is located proximate the outer surface of the catheter tube. The stripe may extend the full length of the catheter tube or may only extend along certain portions which require visualization during an interventional procedure.

Figure 3:
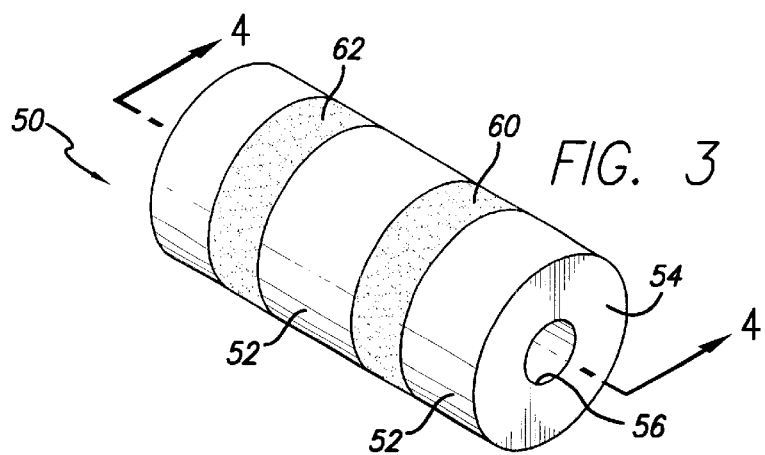
FIG. 3 depicts a partial perspective view of an embodiment of a catheter tube including a plurality of marker bands of the present the invention.
Figure 4:
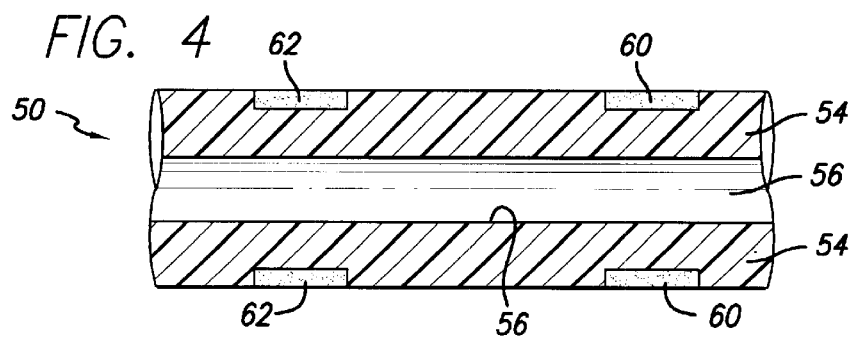
FIG. 4 depicts a cross-sectional view along lines 4—4 of FIG. 3.

Referring now to FIGS. 3 and 4, a catheter tube 50 of the present invention having an outer surface 52, a wall 54 and a lumen 56 is shown. In this alternative embodiment, a plurality of marker bands 62, 60 are shown extending circumferentially around the catheter tube. The marker bands may be embedded within the catheter wall, or may be placed on the outside surface of the wall. These marker bands may be made of any fluorine-19 containing compound as described herein.

Figure 5:
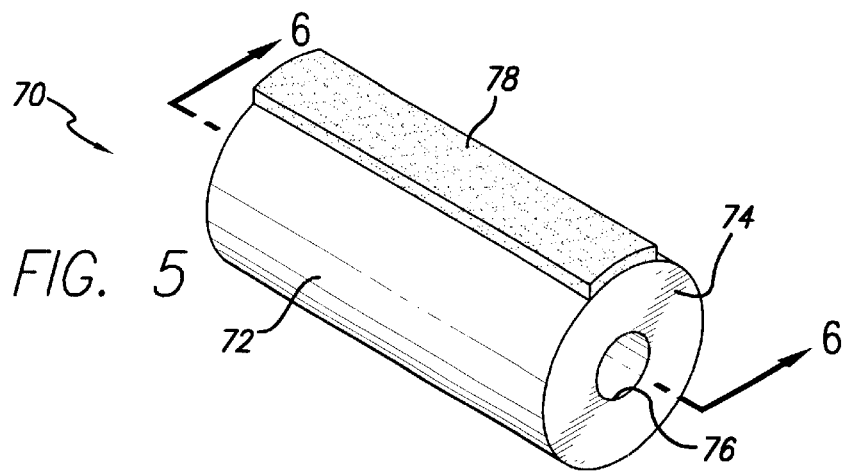
FIG. 5 depicts a partial perspective view of an embodiment of a catheter tube including an external marker stripe of the present the invention.
Figure 6:
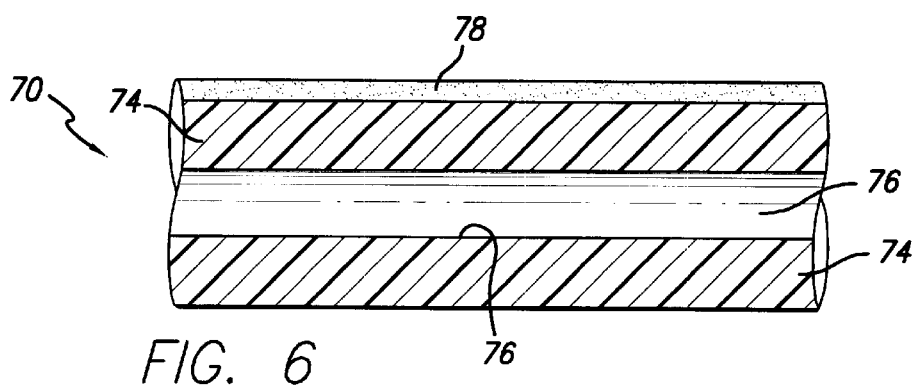
FIG. 6 depicts a cross-sectional view along lines 6—6 of FIG. 5.

Referring now to FIGS. 5 and 6, a catheter tube 70 having a surface 72, a wall 74 and a lumen 76 is shown. This embodiment of the present invention includes a marker stripe 78 located on the outer surface of the catheter tube. The marker stripe may be constructed from any suitable $^{19}$F elastomer as described herein. The marker stripe may be affixed to the catheter tube via gluing, bonding or other similar means.

Figure 7:
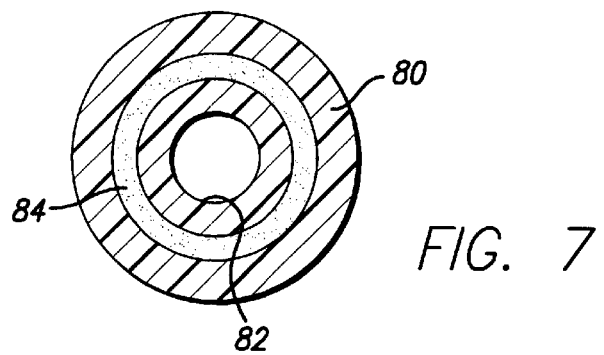
FIG. 7 depicts a transverse cross-sectional view of a catheter tube having an internal marker band.
Figure 8:
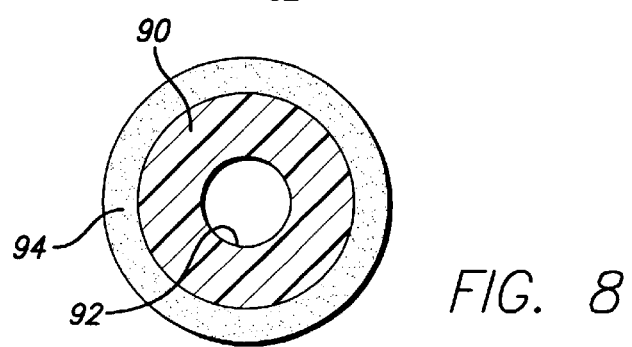
FIG. 8 depicts a transverse cross-sectional view of a catheter tube having an external marker band.

Referring now to FIG. 7, a cross-section of a catheter tube is shown, wherein a marker band 84 is embedded within a wall 80 of the catheter, but not within a catheter lumen 82. As shown in FIG. 8, a marker band 94 is disposed on the outside of a catheter wall 90 having a catheter lumen 92. Alternatively, the marker band or stripe may be included within the catheter lumen.

Figure 9:
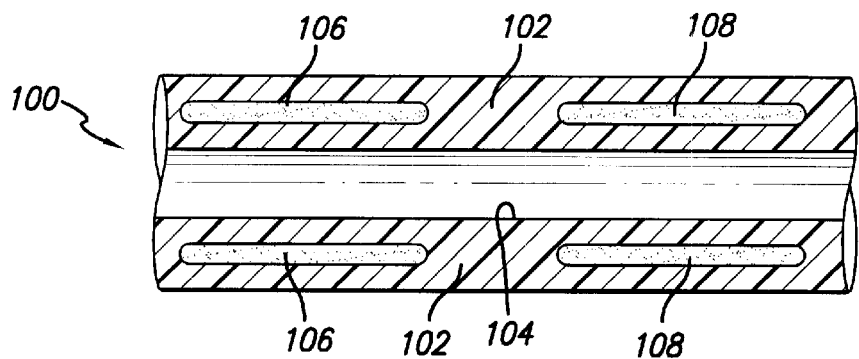
FIG. 9 depicts a longitudinal cross-sectional view of a catheter tube having a plurality of lumens containing passive marker material.
Figure 10:
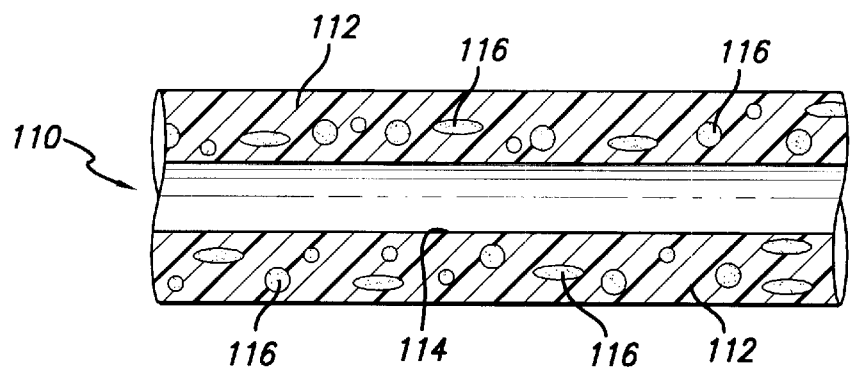
FIG. 10 depicts a longitudinal cross-sectional view of a catheter tube having passive marker material dispersed within the wall of the catheter.

Referring now to FIG. 9, a catheter tube 100 or similar device is shown having a wall 102 and lumen 104. Cylindrical pockets or lumens 106, 108 of perfluorograse, or other fluorine-19 containing material, may be formed in the wall of the catheter, so as to provide one or more marker bands for MR angiography. Alternatively, the pockets of perfluorograse can extend the longitudinal length of the catheter, thereby creating a marker stripe. Alternatively, as shown in FIG. 10, a catheter tubing 110 or similar device may contain multiple pockets or fluid droplets 116 of a perfluorograse or fluorine-19 emulsion within its wall 112 and outside of its lumen 114. Since such greases and emulsions are soft, the $^{19}$F containing materials should be encapsulated in or dispersed into the wall of the catheter or similar device.

Figure 11:
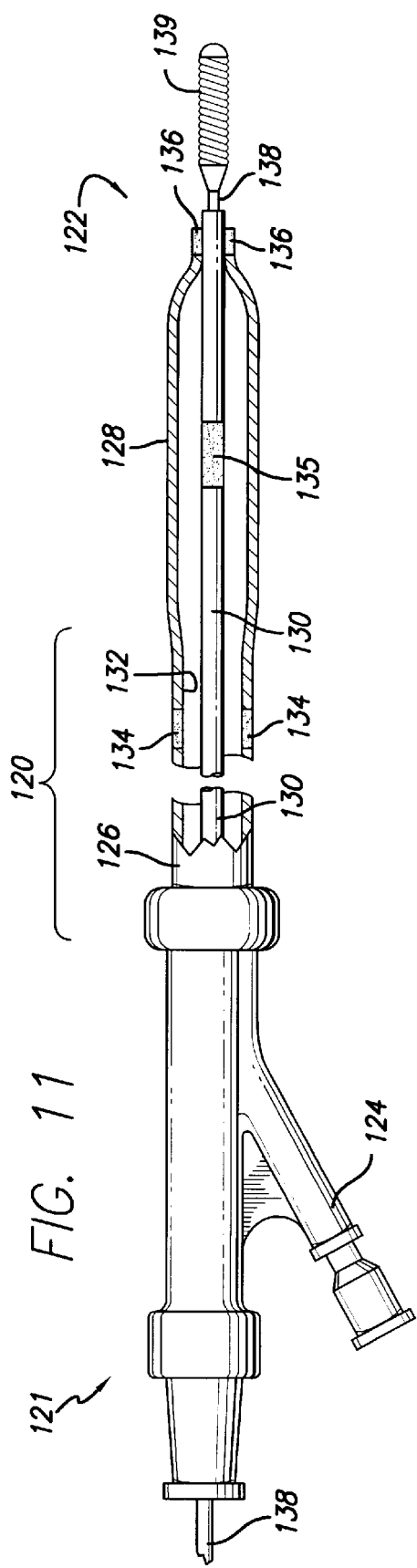
FIG. 11 depicts a longitudinal plan view in partial cross-section of an over-the-wire intravascular catheter assembly including marker bands of the present the invention.

Referring now to FIG. 11, the fluorine-19 markers of the present invention may be incorporated into an over-the-wire (OTW) catheter assembly 120, having proximal portion 121 and distal portion 122. The proximal portion of the catheter assembly may include an inflation port or side arm 124 and catheter tube 126. The distal portion of the catheter assembly may include the catheter tube and a balloon (expandable member) 128 mounted on or secured to the distal end of the catheter tube. The distal portion of the catheter tube is formed with a lumen 132 in which an elongate inner tubular member 130 is disposed. A guidewire 138 may be slidably positioned within the inner tubular member. To enable the visualization of the catheter under MR angiography, one or more marker bands 134, 135 and 136 are provided in the OTW catheter assembly. As by way of example, a marker band 134 is disposed on or within the catheter tube just proximal the balloon. Similarly, a second marker band 136 may be disposed on or imbedded within the distal end of the balloon. Further, a marker band 135 may be disposed on or within the inner tubular member so as to indicate the relative center or other portion of the balloon. Alternatively, as discussed above, the catheter tube may contain an elastomeric stripe, or lumens including perfluorograse or similar fluorine-19 containing emulsion. In addition, the guidewire 138 may contain or be constructed of a fluorine-19 containing material. Similarly, distal end 139 of the guidewire may be made from a perfluorocarbon elastomer or contain a lumen having perfluorograse or emulsion.

Figure 12:
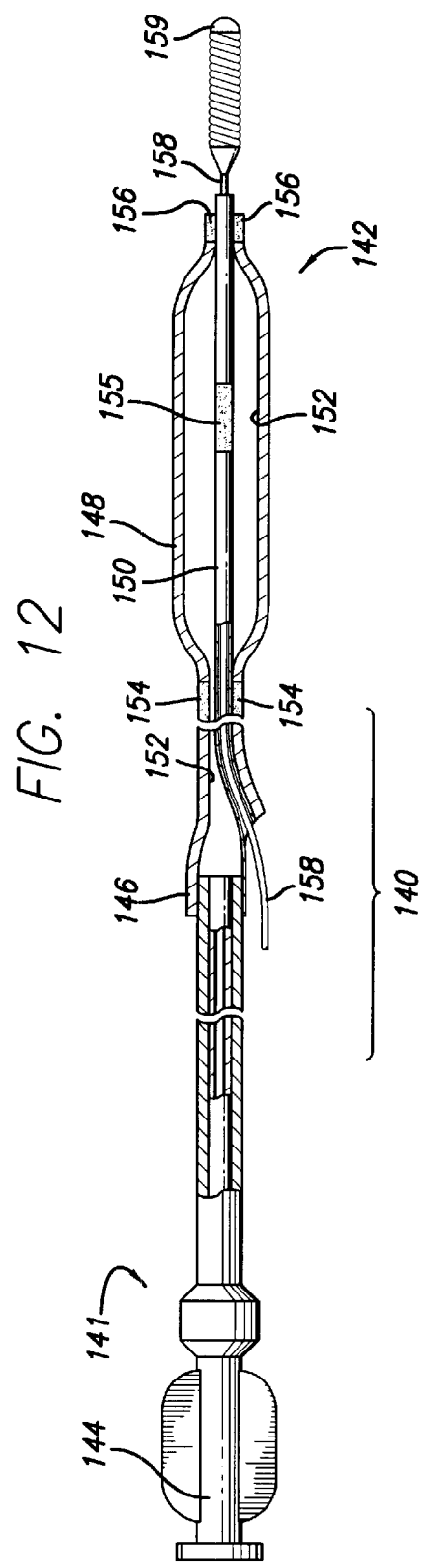
FIG. 12 depicts a longitudinal plan view in partial cross-section of a rapid exchange intravascular catheter assembly including marker bands of the present the invention.

Referring now to FIG. 12, fluorine-19 containing marker bands or similar devices may be included in a rapid exchange (Rx) catheter assembly. The catheter assembly 140 includes a proximal end 141 and a distal portion 142. The proximal end of the catheter may include an inflation port 144. A distal portion of the Rx catheter includes a catheter tube 146, balloon (expandable member) 148 and an elongate inner tubular member 150 included within the lumen 152 of the balloon and tubular member. In accordance with the present invention, the Rx catheter assembly may include one or more marker bands 154, 155 and 156. A first marker band 154 may be disposed on or within the catheter tube just proximal of the balloon. In addition, a second marker band 156 may be included just distal the balloon and along the portion of the catheter tube that joins to the inner tubular member. In addition, a third marker band 155 may be included on or within the inner tubular member and proximate the center of the balloon. As discussed above, the catheter assembly may alternatively include an fluorine-19 containing elastomer stripe, or lumens including a perfluorogrease or emulsion. Further, a guidewire 158 may disposed within the inner tubular member and may contain or be constructed of a fluorine-19 containing material. The distal end 159 of the guidewire may include marker bands, be constructed of an elastomer or other fluorine-19 containing material, or may be embedded with a perfluorogrease or emulsion, as discussed above.

Referring now to FIG. 13, and by way of example, the present invention may be incorporated into a stent or similar endoprosthesis 160. Such a stent may be balloon expandable or self-expanding. Such stents may be made of any suitable biocompatible material, such as AISI 316L stainless steel, nitinol (nickle-titanium alloys) or polymers. Such a stent may be of a ring and link pattern as shown in FIG. 13, or other configurations, such as, but not limited to a zigzag design, a coil design or tubular mesh design, as known in the art or to be determined in the future. By way of example, the stent may include a plurality of marker bands or rings 162, 163 and 164, which include a fluorine-19 compound either included within the structure of the stent or secured to the outside as heretofore described. In addition one or more of the links 166 may contain or be coated with a fluorine-19 containing material.

Referring to FIGS. 14 and 15, the stent 160 may include a fluorine-19 containing material 168 coated, bonded or other wise disposed on the outside of the base material 167 (for example, stainless steel, nitinol or polymer). Conversely, fluorine-19 containing material may be embedded between the base layer 167 and a outer layer 169 of the stent. The outer layer of the stent may be the same material as the base layer, or may be of another material such as a more biocompatible metal, polymer or a drug delivery component.

Referring now to FIGS. 16 and 17, and by way of example, the present invention may be incorporated into an embolic protection device 170. Such device may include a filter assembly 172 and expandable strut assembly 174. The embolic protection device may further include an elongate tubular member 180, within which may be disposed a guidewire 182 for positioning the device within a corporeal lumen. In accordance with the present invention, the embolic protection device may include a plurality of marker bands 186, 187 and 188, which include fluorine-19 containing material. These marker bands may be incorporated into the embolic protection device as heretofore described. In addition, the filter assembly may be constructed from a material such as a perfluorocarbon elastomer, or may contain a dispersion of perfluorogrease or emulsion as heretofore described. Similarly, the expandable strut assembly may include struts 176, 178, which may also contain fluorine-19 containing material or may be constructed from the same. In addition, the guidewire may include or be constructed from a fluorine-19 containing material and the distal end of the guidewire 184 may also include or be constructed from a fluorine-19 containing material.

Figure 18:
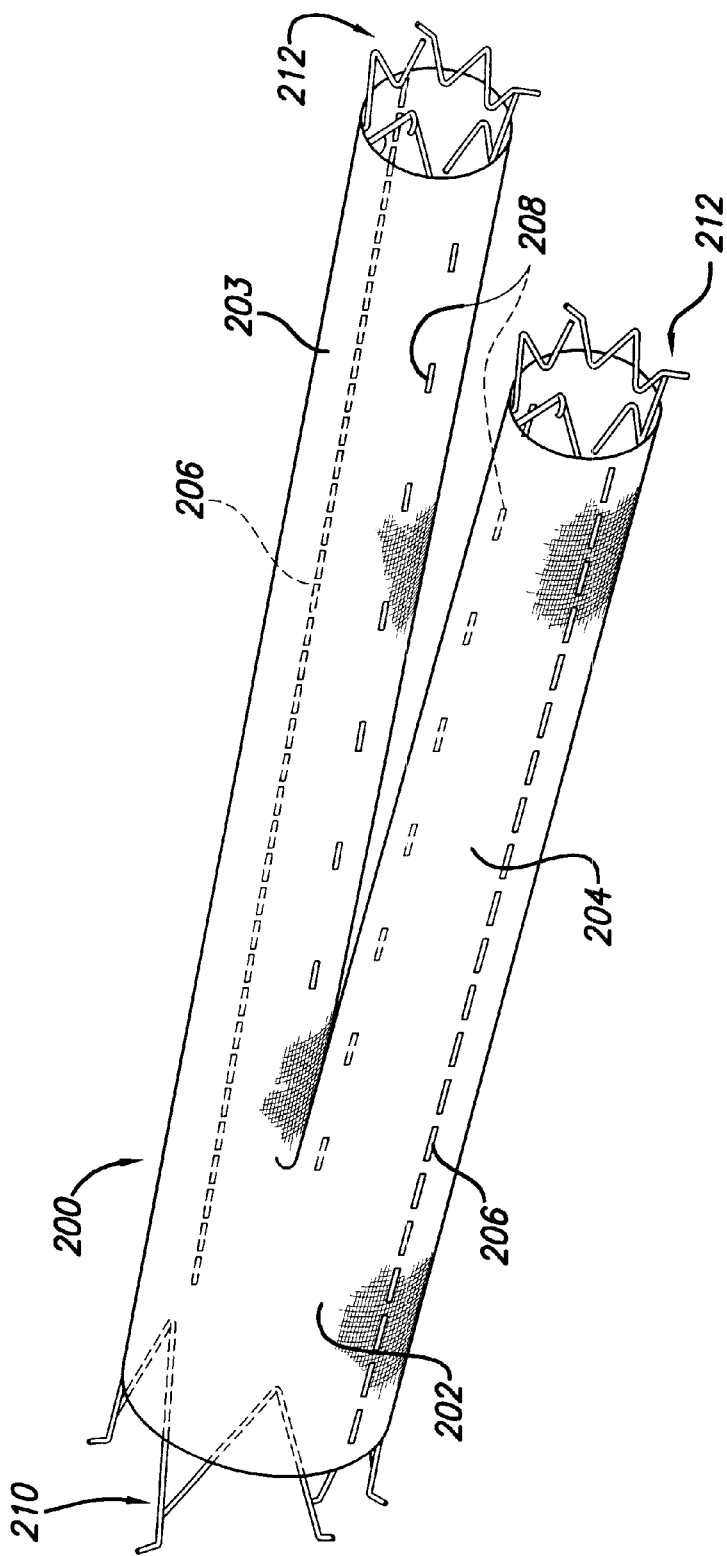
FIG. 18 depicts a perspective view of a graft assembly, including a plurality of marker bands of the present invention.

Referring now to FIG. 18, the fluorine-19 marker system of the present invention may be incorporated into a bifurcated graft 200. Likewise, the marker system may be incorporated into a tubular graft (not shown). Such a graft includes a Dacron, Teflon or other suitable flexible material having an upper body 202, a first leg 203 and a second leg 204, wherein the legs are joined to the upper body. Such a configuration forms a "Y" or "pants leg" configuration. A plurality of closely spaced markers 206 formed from a compound containing a fluorine-19 may be configured on the outside of the first and second legs. Similarly, wider spaced markers 208 may be configured on the inside of the legs of the bifurcated graft (or visa versa). Such markers may be formed from an elastomer or similar fluorine-19 containing material as heretofore described, which may be sewn, glued or otherwise bonded to the graft. In addition, the graft material forming the body and the bifurcated legs may be made of a fluorine 19-containing material or may incorporate such a material. In many such grafts, such as those used for repairing abdominal aortic aneurysms, the upper body may include a first attachment system 210 proximate an upper opening of the graft. Tube grafts may contain a like attachment system at the lower opening of the graft. Similarly, bifurcated grafts may include smaller attachment systems 212 positioned at the end of the legs and proximate the lower openings of the graft. As heretofore described regarding stents (FIGS. 13–15), the attachment system may be made of a variety of materials and may incorporate a fluorine-19 marker system. Such stents and attachment systems may be of various configurations, such as, but not limited to, a ring and link design, a zigzag design, a coil design or tubular mesh design. Also as heretofore described, the attachment systems, like stents, may be coated with or otherwise contain a fluorine-19 marker material and may be further coated with a biocompatible or other desired material.

When combined with a delivery catheter assembly, the fluorine-19 markers of the present invention result in an improved process and method for delivering and implanting a stent or other endoprosthesis to a desired location within a patient's vasculature using interventional magnetic resonance angiography. FIGS. 19 through 22 illustrate, by way of example, a method of delivering and implanting a stent 160 mounted on a balloon 148 of a catheter tube 146, including fluorine-19 containing marker bands 154, 156, 162, 163 and 164. While the drawing figures illustrate a rapid exchange (Rx) intravascular catheter 140 and guidewire 158, embodiments of the fluorine-19 markers of the present invention may be also used with an over-the-wire (OTW) intravascular catheter. Additionally, although the marker system is shown in combination with a balloon expandable stent and associate catheter assembly, the marker system may be used with a self-expanding stent in combination with an appropriate alternative catheter assembly. Likewise, the system may be used in an angioplasty (e.g., PTCA) procedure, without implanting a stent.

The figures illustrate a situation in which the stent delivery catheter having a fluorine-19 marker system is used after an intravascular procedure has created a dissection in the arterial lining to such an extent that the lining needs support to prevent the dissection from collapsing into the arterial passageway and impeding sufficient blood flow through the vessel. In addition, the stent delivery catheter having a fluorine-19 marker system may be used in a balloon angioplasty procedure in which a stent is used to support the vasculature to prevent restenosis. Furthermore, the procedures and devices described herein may be adapted by one of ordinary skill in the art to any procedure where endoprosthesis is to be placed into a body lumen.

As shown in FIG. 19, a catheter assembly 140 is provided with a balloon expandable stent 160 removably secured on an expandable member (balloon) 148 formed on or secured to catheter tube 146. Marker bands 154 and 156 are included on the catheter tube. Alternatively, marker systems as described in FIGS. 1 to 17 may also be used. Further, fluorine-19 markers 162, 163 and 164 are attached to or imbedded within the stent as heretofore described. In addition, a guidewire 158, which may include a marker system, is disposed within the catheter assembly.

Referring to FIG. 20, the catheter assembly is inserted into the lumen of a vessel 190 of a patient's vasculature, such as a coronary artery, and over the guidewire 158 having a distal end 159, which is previously positioned distal to the desired location 194 requiring support. The distal portion of the catheter assembly, including the balloon and stent, is then moved in a distal direction until the balloon and stent are positioned proximate a lesion 192 or stenosis at the desired location of the patient's vasculature.

Figure 21:
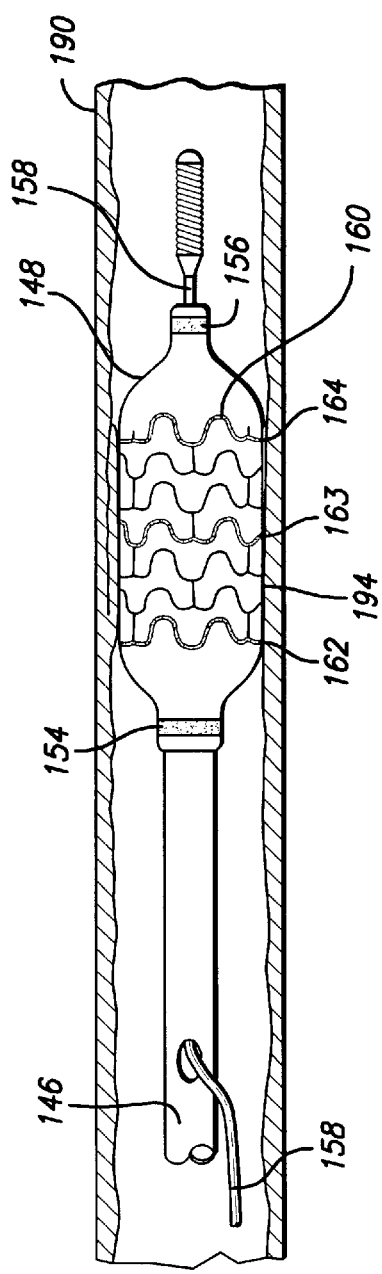
FIG. 21 depicts a longitudinal plan view of a stent delivery catheter assembly, including marker bands of the present invention, which has been positioned proximate a lesion within a cross-section of a patient's vessel, wherein the balloon and stent are fully expanded.
Figure 22:
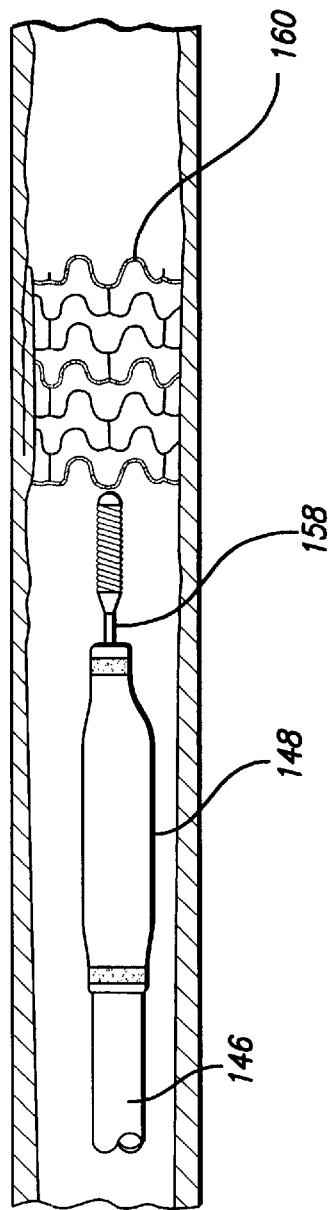
FIG. 22 depicts a longitudinal plan view depicting a partially withdrawn stent delivery catheter assembly, including marker bands of the present invention, wherein a stent has been deployed within a cross-section of a patient's vessel.

As illustrated in FIG. 21, once the stent 160 is positioned at the desired location 194 of the vessel 190, the balloon 148 of the catheter tube 146 is inflated. This may be accomplished, for example, by injecting inflation fluid under substantial pressure into a lumen of the catheter tube. For added contrast, under iMR angiography, the inflation fluid may include a fluorine-19 containing compound, such as described herein. As the balloon expands, the stent also expands, until it is fully expanded and implanted in the vessel. After the stent is fully expanded, the balloon is then deflated or otherwise contracted; however, the expandable stent remains implanted at the desired location in the vessel. Once the stent is no longer in contact with the catheter assembly, then the catheter, balloon and guidewire 158 are withdrawn from the vasculature (FIG. 22).

The dimensions of the intravascular catheter will generally follow the dimensions of intravascular catheters used in angioplasty procedures in the same arterial location. Typically, the length of a catheter assembly for use in the coronary arteries is about one hundred and fifty centimeters, the outer diameter of the catheter expandable member is about 0.89 millimeters, the length of the balloon is typically about two centimeters and the inflated diameter of the balloon is about one to about eight millimeters, depending upon the application. Catheter dimensions for peripheral use will vary, and is known in the art. The materials of construction of the catheter assembly, catheter tube and expandable member may be selected, for example, from those used in conventional balloon angioplasty catheters. Furthermore, the specific dimensions and materials of construction of the detachable sheath are provided as examples, and substitutes are readily contemplated which do not depart from the invention.

While the present invention has been described herein in terms of delivering an expandable stent to a desired location within a patient's blood vessel, the delivery catheter can also be employed to deliver stents to locations within other body lumens so that the stents can be expanded to maintain the patency of those body lumens. In addition, the detachable sheath may be used to removably secure self-expanding stents to delivery catheters.

While particular forms of the invention have been illustrated and described, it will also be apparent to those skilled in the art that various modifications can be made without departing from the spirit and scope of the invention. More specifically, it should be clear that the present invention is not limited to catheters, tubular type stents or embolic protection devices. Likewise, the invention is not limited to any particular method of forming the underlying medical device structure. Accordingly, it is not intended that the invention be limited, except as by the appended claims.

What is claimed is:

1. A medical device for use in a interventional magnetic resonance angiography, comprising a compound containing fluorine-19.

2. The medical device of claim 1, wherein the compound containing fluorine-19 is an elastomer.

3. The medical device of claim 1, wherein the compound containing fluorine-19 is a fluid.

4. The medical device of claim 1, wherein the compound containing fluorine-19 is a fluorosilicone.

5. The medical device of claim 1, wherein the compound containing fluorine-19 is a perfluorocarbon grease.

6. The medical device of claim 1, wherein the compound containing fluorine-19 is an elastomer selected from the group consisting of CHEMRAZ, VITON, KEL-F, KALREZ, FLUOREL, copolymers of vinylidene fluoride and hexafluoropropene, copolymers of chlorotrifluoroethylene and vinylidene fluoride, poly (trifluoropropylmethylsiloxane), fluorosilicone elastomers, polymethyl-3,3,3-trifluoro-propylsiloxane, polymethyl-3,3,3-trifluoropropyl-dimethylsiloxane copolymer and perfluororesins.

7. The medical device of claim 1, wherein the compound containing fluorine-19 is a fluid selected from the group consisting of FLUORONOZ, TRIFLUNOX, FOMBLFN, GALDEN, perfluoropolyether grease, trifluoropropylsilicone fluids, fluorosilicone fluids, perfluoropolyether fluids, perfluoroalkylether fluids, perfluoroalkanes, perfluoropropane, perfluorobutane, perfluoropentane, perfluorohexane, perfluoroheptane, perfluorooctane, perfluorononane, perfluorodecane, perfluorocarbon emulsions, perfluoroalkylpolyester oils, perfluoropolyether solvent, fluorine containing freons, chlorofluorocarbons and hydrochlorofluorocarbons.

8. A medical device, comprising means for visualizing under magnetic resonance angiography, wherein the means for visualizing includes a compound containing fluorine-19.

9. The medical device of claim 8, wherein the compound containing fluorine-19 is an elastomer having a fluorine-19 concentration in the range of 15 to 125 moles/liter.

10. The medical device of claim 8, wherein the compound containing fluorine-19 is a fluid having a fluorine-19 concentration in the range of 15 to 125 moles/liter.

11. The medical device of claim 8, wherein the means for visualizing forms a marker band.

12. The medical device of claim 8, wherein the means for visualizing forms a marker stripe.

13. The medical device of claim 8, wherein the means for visualizing is dispersed within the medical device.

14. A catheter assembly, comprising:
 a catheter tube having wall, an outer surface, a proximal end portion and a distal end portion; and
 a marker formed from fluorine-19 containing material.

15. The catheter assembly of claim 14, wherein the marker is a stripe formed within the wall of the catheter tube.

16. The catheter assembly of claim 14, wherein the marker is a stripe formed on the outer surface of the catheter tube.

17. The catheter assembly of claim 14, wherein the marker is a band formed within the wall of the catheter tube.

18. The catheter assembly of claim 14, wherein the marker is a band formed on the outer surface of the catheter tube.

19. The catheter assembly of claim 14, wherein the marker is dispersed within the wall of the catheter tube.

20. The catheter assembly of claim 14, further including an expandable member associated with the distal end portion of the catheter, wherein a marker containing fluorine-19 material is formed within the expandable member.

21. A balloon catheter assembly, comprising:
a catheter tube having wall, an outer surface, a proximal end portion and a distal end portion;
an expandable member associated with the distal end portion of the catheter;
a first marker having fluorine-19 containing material formed on the catheter tube and positioned proximal of the expandable member; and
a second marker having fluorine-19 containing material formed on the catheter tube and positioned distal of the expandable member.

22. The catheter assembly of claim 21, further including an elongate tubular member disposed within the expandable member and having a marker with fluorine-19 containing material.

23. An endoprosthesis for implanting in a body lumen, comprising a body having an outer surface, the body including a compound containing fluorine-19 positioned proximate the outer surface.

24. A stent, comprising a body having an outer surface, the body including a compound containing fluorine-19 positioned proximate the outer surface.

25. The stent of claim 24, further comprising plurality of struts including a compound containing fluorine-19.

26. An embolic protection device, comprising a filter having an outer surface, the filter including a compound containing fluorine-19 positioned proximate the outer surface.

27. The embolic protection device of claim 26, further comprising an elongate tubular member including a marker formed from a compound containing fluorine-19.

28. The embolic protection device of claim 27, further comprising plurality of struts including a compound containing fluorine-19.

29. A graft, comprising a body including a marker formed from a compound containing fluorine-19.

30. The graft of claim 29, further comprising:
a first leg in fluid communication with the body and having at least one marker formed from a compound containing fluorine-19; and
a second leg in fluid communication with the body and having at least one marker formed from a compound containing fluorine-19.

31. A method of performing angioplasty using magnetic resonance angiography, the method comprising:
providing a catheter assembly including,
a catheter tube having a proximal end portion and a distal end portion,
an expandable member formed on the distal end portion of the catheter tube,
at least one marker having fluorine-19 containing material formed on the catheter tube and positioned proximate the expandable member, and
advancing the distal end portion of the catheter and the expandable member to a desired location in a patient vasculature having a stenosis;
visualizing vasculature, stenosis and the fluorine-19 containing material through magnetic resonance angiography;
expanding the expandable member so as to expand the stenosis and open the vasculature;
contracting the expandable member; and
withdrawing the catheter and the expandable member from the patient vasculature.

32. The method of claim 31, further comprising using a fluorine-19 containing contrast agent when expanding the expandable member, and visualizing the contrast agent through magnetic resonance angiography.

33. A method of delivering a stent into a desired location within a patient's vasculature, the method comprising:
providing a catheter assembly including,
a catheter tube having a proximal end portion and a distal end portion,
a balloon formed on the distal end portion of the catheter tube, and
a stent disposed on the balloon and configured with a body having an outer surface, the body including fluorine-19 containing material positioned proximate the outer surface;
advancing the distal end portion of the catheter tube, the balloon and the stent though the vasculature to a desired location;
visualizing the fluorine-19 containing material through magnetic resonance angiography;
inflating the balloon so as to expand the stent into the desired location;
deflating the balloon; and
withdrawing the catheter tube and the balloon from the vasculature.

34. The method of claim 33, further comprising using a fluorine-19 containing contrast agent when inflating the balloon, and visualizing the contrast agent through magnetic resonance angiography.

35. The method of claim 33, further comprising providing a first marker having fluorine-19 containing material formed on the catheter tube and positioned proximal of the balloon, providing a second marker having fluorine-19 containing material formed on the catheter tube and positioned distal of the expandable member, and visualizing the fluorine-19 containing material formed on the catheter tube through magnetic resonance angiography.

36. A stent, comprising a body formed from a base material having an outer surface, the body further including a compound containing fluorine-19.

37. The stent of claim 36, wherein the compound containing fluorine-19 is an elastomer.

38. The stent of claim 37, wherein the elastomer is disposed on the outer surface of the base material.

39. The stent of claim 37, wherein the elastomer is disposed between the outer surface of the base material and an outer layer of the body.

40. The stent of claim 36, wherein the compound containing fluorine-19 is a fluorosilicone.

41. The stent of claim 40, wherein the fluorosilicone is disposed on the outer surface of the base material.

42. The stent of claim 40, wherein the fluorosilicone is disposed between the outer surface of the base material and an outer layer of the body.

43. The stent of claim 36, wherein the compound containing fluorine-19 is a fluid.

44. The stent of claim 43, wherein the fluid is dispersed within the base material.

45. The stent of claim 36, wherein the compound containing fluorine-19 is a perfluorocarbon grease.

46. The stent of claim 45, wherein the perfluorocarbon grease is dispersed within the base material.

* * * * *